United States Patent [19]

Bojanic et al.

[11] Patent Number: 5,417,923
[45] Date of Patent: May 23, 1995

[54] ASSAY TRAY ASSEMBLY

[75] Inventors: Dejan Bojanic; James R. Merson, both of Kent, England

[73] Assignee: Pfizer Inc., New York, N.Y.

[21] Appl. No.: 182,956

[22] Filed: Jan. 18, 1994

Related U.S. Application Data

[63] Continuation of Ser. No. 965,839, Oct. 20, 1992, abandoned, which is a continuation of Ser. No. 690,740, Apr. 24, 1991, abandoned.

[51] Int. Cl.⁶ ............................................. B01C 11/00
[52] U.S. Cl. ................................... 422/101; 422/70; 422/102; 435/300; 435/311
[58] Field of Search ............... 422/101, 102, 70, 68.1; 435/284, 300, 301, 311; 210/238

[56] References Cited

U.S. PATENT DOCUMENTS

| | | | |
|---|---|---|---|
| 4,895,706 | 1/1990 | Root et al. | 422/102 |
| 4,902,481 | 2/1990 | Clark et al. | 422/101 |
| 5,035,866 | 7/1991 | Wannlund | 422/102 |
| 5,264,184 | 11/1993 | Aysta et al. | 422/101 |

*Primary Examiner*—Robert J. Warden
*Assistant Examiner*—Krisanne M. Thornton
*Attorney, Agent, or Firm*—Peter C. Richardson; Gezina Holtrust; B. Timothy Creagan

[57] ABSTRACT

An assay tray assembly and an assay tray primarily for chromatographic analysis has a plastics moulded test tray 1 mounted on a plastics moulded collection tray 72, The test tray has a spaced array of chambers 3 disposed as per a microtiter plate, Each chamber has a bottom outlet port 5 formed by a flange 8 which retains within the chamber a chromatographic medium to which test liquid deposited in the chamber is to be subjected for the percolate or eluate liquid to emerge from the respective outlet ports, The collection tray 72 has a spaced array of wells 16 disposed as per a microtiter plate to correspond with the chambers 3 and the tray 14 is mounted on the tray 72 for each chamber to communicate with a corresponding well 16. Each chamber 3 has a tubular spigot part 12 which extends into the respective well 16 to alleviate cross contamination of the liquid derived from the outlet ports 5.The depth of entry of the tubular spigots 12 into their respective wells 16 is restricted by abutment between the bottom of the test tray with the top of the collection tray, The volume of each well 16 beneath the tubular spigot it receives is adequate to accommodate all of the eluate or percolate derived from the chamber 3 with which it communicates to alleviate liquid on the spigot parts from dripping into wells with which those tubular spigots are not associated (and thereby cause cross contamination) when the trays are separated for analysis of the percolate or eluate.

6 Claims, 2 Drawing Sheets

ASSAY TRAY ASSEMBLY

This is a continuation of application Ser. No. 07/965,839, filed on Oct. 20, 1992, now abandoned, which was a continuation of application Ser. No. 07/690,740, filed on Apr. 24, 1991, now abandoned.

TECHNICAL FIELD AND BACKGROUND ART

The present invention relates to an assay tray assembly. It is particularly concerned with an assembly for use in the testing or analysis of liquids, usually of a chemical, bio-chemical or biological nature, by a batch process whereby multiple small quantities of the liquid or liquids under test can be prepared for analysis substantially simultaneously, the process conveniently being carried out by conventional mechanical handling equipment. Assemblies of the kind mentioned include an separation medium to which the liquid for analysis is subjected; this medium may simply serve to remove solid/particulate matter from the liquid by filtration or may be in the form of chromatographic medium having a selectively adsorbent nature intended to separate or indicate a particular characteristic (or the lack of such a characteristic) of the liquid under test.

Particularly in chemical and pharmaceutical research there is a large demand for the assay or analysis of small quantities of liquid by chromatographic techniques and it has hitherto been proposed to provide array trays and assemblies whereby individual samples of test liquid are prepared for and subjected to analysis by multi-batch processing on a microtiter principle, for example as disclosed in EP-A-2-0087899 in which samples of a reaction medium are carried by a spaced array of downwardly extending rods which rods and samples are inserted, one each, into a corresponding array of discrete wells containing the test liquid. An assay tray assembly for similar batch processing is also disclosed in U.K. Patent Specification No. 2,188,418A in which a base tray has a plurality of reaction wells and an overlying tray has a corresponding number of solid or hollow reaction projections either or both of which may carry a reaction medium that provides a basis for analysis when the reaction projections are inserted into the corresponding reaction wells containing the test liquid.

A conventional assay technique is to locate the separation medium in an upstanding tubular chamber having an open top and a bottom outlet and to pipette or otherwise deposit the liquid under test into the chamber to flow through or over the extraction medium prior to emerging from the bottom outlet. Conventionally this type of analysis is made on an individual basis, for example by use of an extraction cartridge sold under the Trade Mark BOND ELUT which comprises a tubular plastics body carried within which is a predetermined chromatographic medium. Such individual cartridges have been found inappropriate in trying to achieve a high through put of test samples for analysis. It has however been proposed, in U.S. Pat. No. 4,090,850 to provide an assay unit (particularly for radio-immunio assay) which utilizes a batch process whereby a tray is provided with multiple wells each having at its bottom an outlet communicating with a vacuum chamber. Each well carries an extraction medium so that liquid under test deposited in each well flows through the extraction medium and the percolate or eluate, as the case may be, passes by way of the outlets into the vacuum chamber which acts as a common waste reservoir. By exhausting the vacuum chamber the liquids in the wells are subjected to a pressure differential to increase the rate of through-flow for the analysis procedure.

With assay techniques in which there is a flow of liquid under test through or over a separation medium as previously discussed, it is frequently important that the liquid emerging from the separation medium is available for discrete analysis, possibly as an alternative, or addition, to the analysis of the separation medium. If such a facility is to be provided in the assaying of liquids by use of a batch technique, it is essential that there is no intermixture or cross contamination between the liquids emerging from the individual outlets of the several chambers which accommodate the separation medium. It is an object of the present invention to provide an assay tray assembly by which this requirement may be satisfied and which may be produced relatively inexpensively for one-lime or repeated use, is convenient to use, and lends itself to mechanical handling and processing, for example with apparatus having an automatic bulk dispensing and aspirating capability.

STATEMENTS OF INVENTION & ADVANTAGES

According to the present invention there is provided an assay tray assembly comprising a plastics moulded test tray removably mounted in overlying relationship in engagement with a plastics moulded collection tray; the test tray having a spaced array of discrete identical upstanding chambers to accommodate a predetermined volume of liquid for analysis, each chamber being formed with a top opening and a bottom opening for the flow therethrough of the liquid, said bottom opening being located in a downwardly projecting tubular spigot for the respective chamber and each said chamber carrying a separation medium to which the liquid is to be subjected during its said through-flow the collection tray having discrete upstanding wells each with an upwardly opening mouth, said wells corresponding in number to the chambers and having their mouths disposed in a spaced array corresponding to that of the tubular spigots the tubular spigots being received one in each of said well mouths for the respective wells to collect liquid emanating from the chambers and to alleviate cross contamination between such liquids and wherein abutment means is provided between the trays to restrict the depth of entry of the tubular spigots into the wells whereby the volume of each well below the tubular spigot it receives is greater than the volume of a liquid which it is intended to receive from the chamber communicating therewith.

By the present invention the tubular spigots of the chambers are received, or intended to be received, one each in the mouths of discrete wells in a collection tray. This ensures that the liquid (or liquids) which is under test will flow over or through the separation medium and by way of the opening in the bottom of its respective chamber into a particular well of the collection chamber without unintentional seepage or cross contamination of such liquid between the adjacent chambers or wells. Furthermore, in the assembly of the invention it is intended that the volume of each well is capable of accommodating below the tubular spigot with which it communicates, all of the liquid (the percolate or eluate) which passes through the tubular spigot and is derived from the liquid initially deposited in the corresponding chamber. It is envisaged that the liquid under test will usually be pipetted into the chambers in predetermined volumes, possibly to the extent that a particular chamber is full of such liquid above the separation medium and the volume of the well should be capable of accommodating an equivalent volume of liquid below and out of contact with the tubular spigot. By ensuring that when the test and collection trays are fitted together with the tubular spigots engaging in the respective wells and each well has adequate capacity to accommodate, beneath the tubular spigot, the whole of the liquid through flow, it will be appreciated that such liquid is remote from the separation medium and the tubular spigots and the possibility is alleviated of liquid seeping from one well to another and possibly dripping from the spigots to cause cross contamination when the two trays are separated. The samples of liquid in the wells can therefore confidently be subjected to independent analysis.

The trays are preferably formed as one piece injection mouldings with their respective chambers and wells disposed in a conventional microtiter plate layout, that is arrayed in columns and rows extending perpendicularly thereto. A typical such array has twelve parallel columns and eight parallel rows to provide ninety six chambers or wells in the respective trays (this latter array is likely to prove most acceptable for automatic handling of the trays by multiple batch piperring equipment which is currently available). The trays will usually have moulded-in indicia for individually identifying each chamber or well as the case may be and similar indicia will normally be provided for both the test tray and the collection tray. Orientating means may be provided which permits engagement between the two trays only when they are mounted in their correct overlying relationship in which it is ensured that the two trays are correctly orientated with respect to each other (that is when the individually identified tubular spigots engage within correspondingly individually identified wells). The orientating means can conveniently comprise moulded-in tracks, projections, recesses or rebates on the trays which are intended to inter-engage between the trays when the trays are correctly mounted (or possibly to engage with mechanical handling equipment to ensure that the test and collection trays are correctly orientated with respect to each other and in the equipment) prior to the chambers being charged with the liquid under test.

The chambers are preferably formed by downwardly extending tubes in a substantially parallel array which tubes may be maintained in their spaced array by upstanding webs of the test tray that interconnect each such tube to the tubes adjacent thereto. Similarly it is preferred that the wells comprise a substantially parallel array of tubular walls having closed bottom ends and which tubular wells may be maintained in their spaced array by upstanding webs that interconnect each of the tubular wells to the tubular wells adjacent thereto. The webs advantageously reinforce the trays and maintain rigidity for the tubular walls (which may be particularly desirable when the trays are to be subjected to shock forces, for example, by centrifuging).

The depth of entry of the tubular spigots on the test tray into the wells of the collection tray is conveniently restricted by abutment of bottom edges of the aforementioned webs of the test tray on the top of the collection tray. The test tray may have a downwardly extending peripheral wall that extends around the chambers and the depth of entry of the tubular spigots into the wells may also, or alternatively, be restricted by abutment of a lower end of said peripheral wall with the top of the collection tray. The bottom end of the peripheral wall may be rebated to provide a skirt within which is accommodated a substantially corresponding profile on an upper surface of the collection tray so that the collection tray is received as a reasonably good fit within the skirt of the test tray.

The tray assembly of the present invention was primarily developed for chromatographic assay purposes and in this context an appropriate chromatographic medium will be carried within each chamber and retained therein from being flushed through the bottom opening with the test liquid. Conveniently the chromatographic medium is retained in the chamber by an internal shoulder on a wall of the chamber, such shoulder underlying the medium. Each chamber preferably has a circular section to be of cylindrical or frusto conical form (the latter tapering to converge towards the bottom opening in the tubular spigot) and a small annular flange may be provided at the bottom end of each tubular spigot to provide the shoulder for restraining the chromatographic medium as aforementioned. The chromatographic medium selected may be of a form conventional for the extraction cartridges sold under the Trade Mark BOND ELUT by Analytichem International and may be sandwiched within the chamber between underlying and overlying frits which are usually of a porous nature. Typically the frits are nylon or sintered discs which serve to retain the medium in position within the chamber and provide filtering characteristics. It is preferred that at least the part length of the chamber within which the chromatographic or other separation medium is accommodated has a substantially constant cross-section, conveniently of cylindrical profile, such that face-to-face contact occurs between the aforementioned frits and the chamber wall, or when a relatively rigid or non-resilient cylindrical slug of the separation medium is used, to ensure a reasonable length of face-to-face contact is provided between the medium and the chamber wall. The provision of the relatively long, conveniently cylindrical, contact faces is to alleviate difficulties which have been encountered where the frits and/or the chromatographic medium are of a relatively rigid or non-resilient material and a cylindrical slug of such a material when located in a frusto conical chamber provides only a narrow circular line of contact therewith (this contact may be inadequate to maintain the material in position and may also permit seepage of the test liquid between the material and the wall of the chamber). A constant cross section of the chamber also alleviates any need to use frits of different dimensions in different part lengths of the chamber.

BRIEF DESCRIPTION OF THE DRAWINGS

One embodiment of an assay tray assembly constructed in accordance with the present invention will now be described, by way of example only, with reference to the accompanying illustrative drawings, in which.

DETAILED DESCRIPTION OF DRAWINGS

Figure 1:
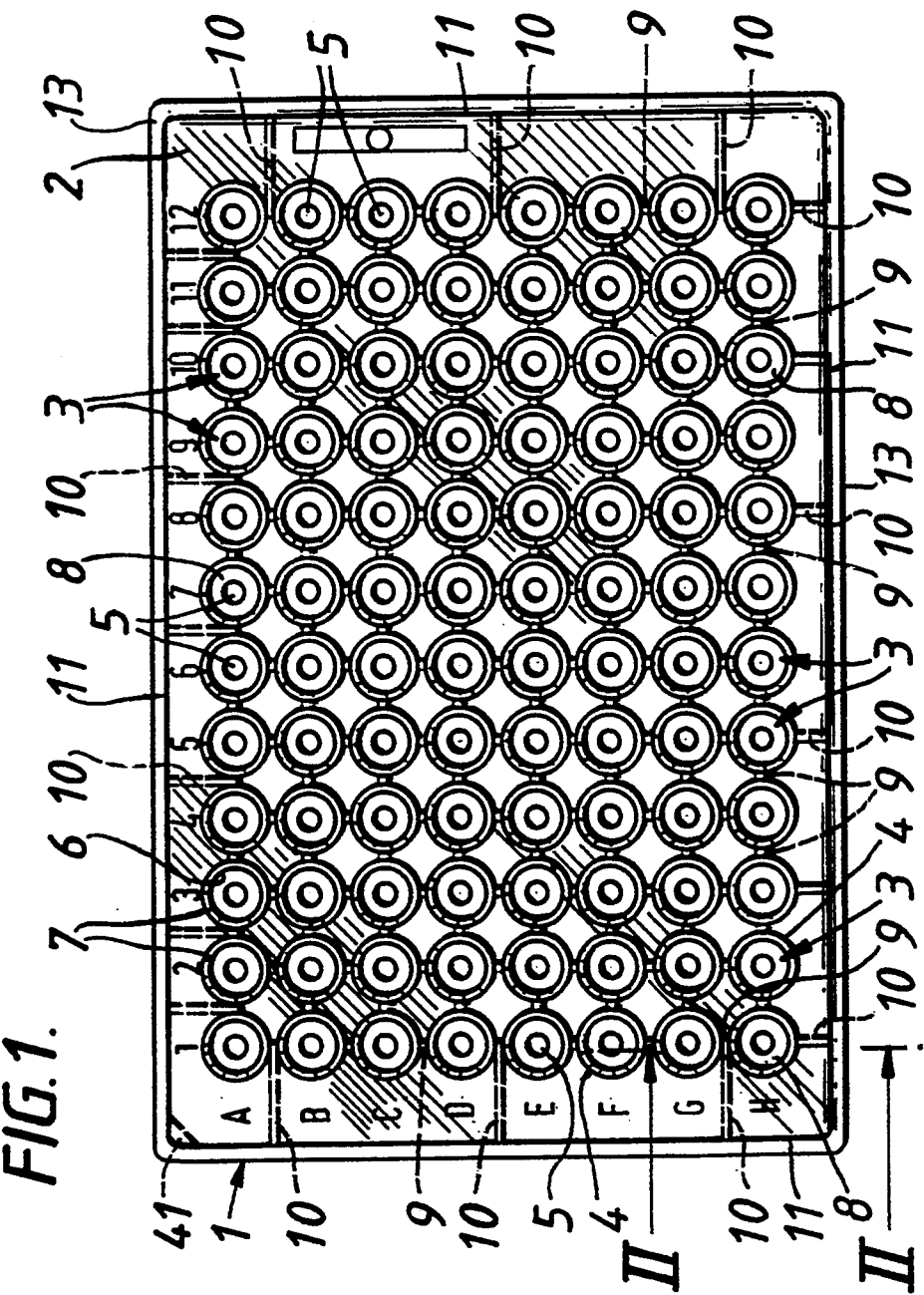
FIG. 1 is a plan view of the assay test tray removably mounted on a collection tray in accordance with the invention.

The assay tray assembly illustrated has a test tray 1 and a collection tray 72 each of which is a one piece unit injection moulded in plastics. The test tray 1 has an oblong rectangular and flat upper wall surface 2 opening into which are ninety six chambers 3 disposed in a spaced array similarly to a conventional microtiter plate. In this array there are eight rows extending parallel to a longer side edge of the face 2 with twelve chambers 3 in each row and the chambers are spaced to provide twelve parallel columns with eight chambers in each column extending perpendicularly to the rows. The rows are identified by the letters A to H shown in FIG. 1 and the columns by the numerals 1 to 12 shown in FIG. 1, these letters and numerals are moulded into the surface 2 so that by reference thereto each chamber may be individually identified. The chambers 3 are identical and parallel to each other and each is formed by a tubular wall 4 extending downwardly from the top opening thereof in the upper wall 2 to provide a bottom opening or outlet port 5. The lower part length 6 of each chamber 3 is cylindrical and communicates with a co-axial frusto conical upper part length 7 which tapers to converge from the top opening to the cylindrical chamber part 6. The outlet port 5 is formed by an annular flange 8 at the bottom end of the tubular wall 4 and which provides a shoulder within the chamber 3. The tubular walls 4 are maintained in their spaced array by their moulding into the upper wall 2, by upstanding webs 9 which interconnect each tubular wall 4 to the tubular walls 4 adjacent thereto and also by a spaced array of upstanding webs 10 which interconnect the webs 9 (and possibly the tubular walls 4) to a peripheral side wall 11. The side wall extends downwardly from the periphery of the upper wall 2 and Surrounds the array of tubular walls 4 in the test tray. The webs 9 and 10 serve to reinforce the structure of the tray and their form will be apparent to persons skilled in the art of injection moulding.

Figure 2:
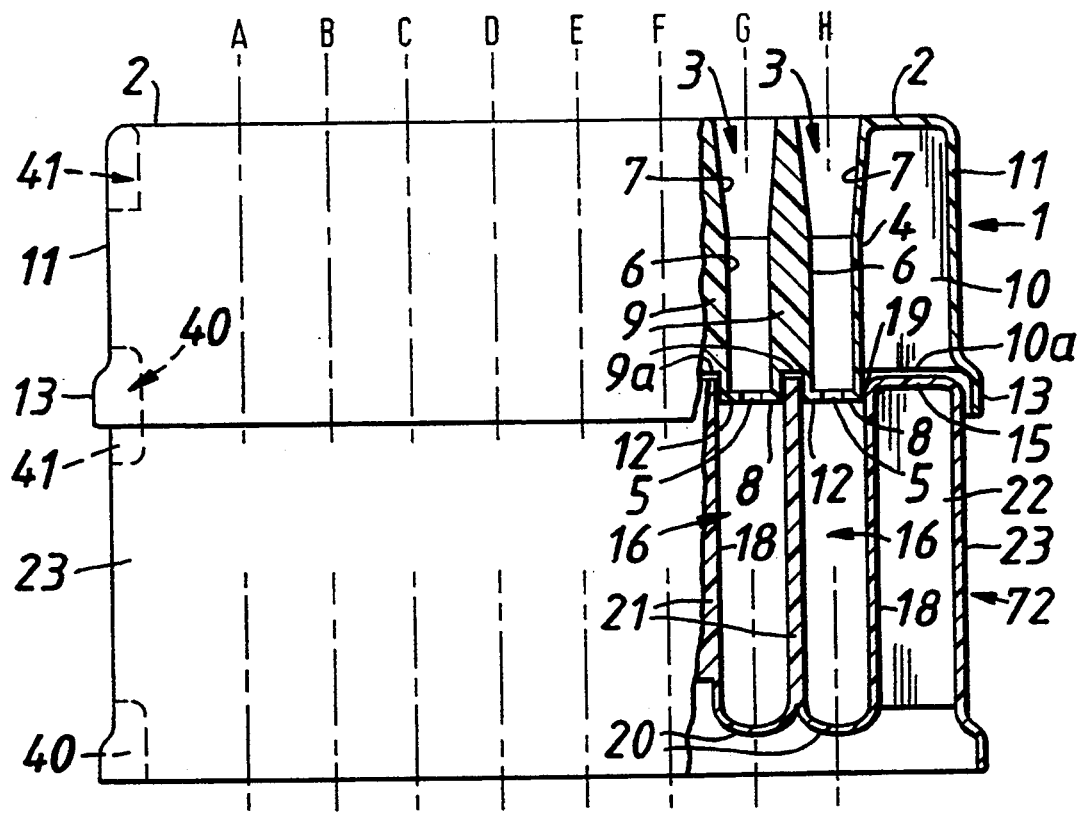
FIG. 2 is a side view of the assembly shown in FIG. 1 and shows the assembly in part section taken on the line II—II of FIG. 1.
Figure 3:
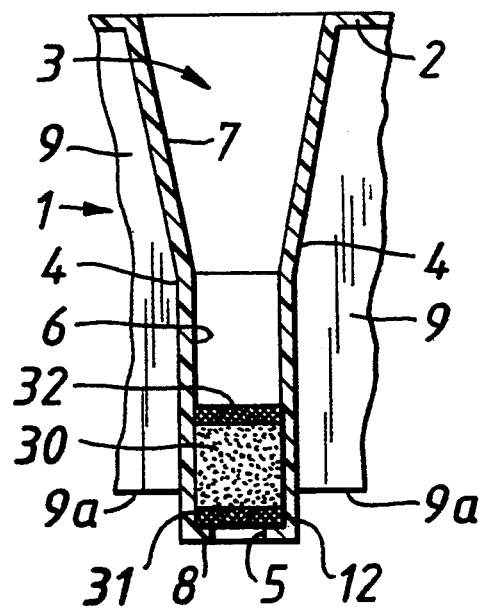
FIG. 3 is an enlarged sectional view of a chamber in the test tray of the assembly with the chamber accommodating a chromotographic medium.

It will be seen from FIGS. 2 and 3 that the bottom part length of each tubular wall 4 for a chamber projects downwardly beyond the lowermost edges 9a and 10a of the webs 9 and 10 respectively to form tubular spigots 12. The bottom end of the peripheral wall 11 is formed as a peripheral skirt 13 which extends downwardly beyond the lowermost edges 9a and 10a similarly to the tubular spigots 12.

The collection tray 72 has an upper wall surface 15 opening into which is a spaced array of ninety six wells 16. The wells 16 are identical to each other and disposed in rows and columns which correspond to the rows and columns of the chambers 3 (particularly with respect to the tubular spigots 12). The upper surface 15 has (not shown) moulded-in identification letters A to H and numerals 1 to 12 in a similar manner to the test tray 1 so that each individual well 16 can readily be identified by reference to the indicia letters and numerals. The profile of the surface 15 corresponds to that of the surface 2. Each well is formed by a cylindrical tubular wall part 18 which forms a mouth 19 in the upper wall 15 from which it extends downwardly and the bottom end of the well is closed by a hemispherical wall part 20. The well walls 18 are retained in their spaced array and in parallel relationship with each other by the upper surface wall 15, upstanding webs 21 which interconnect each tubular wall 18 with the tubular walls 18 adjacent thereto, and upstanding webs 22 which interconnect the webs 21 (or possibly the walls 18) with a peripheral side wall 23 of the collection tray. The webs 21 and 22 are similar to the webs 9 and 10 and the peripheral side wall 23 extends downwardly from the upper surface wall 15 to surround the wells. For convenience in FIG. 2 the sectioned part illustrates chambers 3 and wells 16 in columns G and H only—it being appreciated that chambers and wells are similarly provided in the rows indicated at A to F.

In use it is intended that the test tray 1 will be mounted in overlying relationship on the collection plate 72 with the upper wall surfaces 2 and 15 similarly orientated for the reference letters A to H and reference numerals 1 to 12 to correspond in directly overlying relationship. In such mounting the trays engage for the skirt 13 of the test tray 1 to receive the upper surface 15 of the collection tray 72 in substantially complementary manner while the tubular spigots 12 are received within the mouths 19 of the corresponding wells 16 as shown in FIG. 2. The depth to which the tubular spigots 12 enter the wells 16 is determined by the abutment of the lower edges 9a and 10a of the webs in the test tray on the upper wall surface 15 of the collection tray. Alternatively, or in addition, the depth of insertion of the tubular spigots can be restricted by abutment of the peripheral edge of the upper wall surface 15 against an internal shoulder formed by the skirt 13 on the test tray.

For the purpose of conducting an assay a selective separation medium will be carried in each of the chambers 3 of the test tray. Liquid under analysis is intended to flow over or through the separation medium and pass from the outlet ports 5 to be deposited in the wells 16 with which the tubular spigots 12 respectively communicate. The tray assembly and test tray 1 illustrated are primarily intended for use in conducting a chromatographic assay and a selective chromatographic medium is located in each of the chambers 3 in a similar manner to the previously mentioned known extraction cartridges sold under the Trade Mark BOND ELUT. For convenience the chromatographic medium has been omitted from the test tray in FIGS. 1 and 2 but such a medium is shown at 30 in the chamber 3 of FIG. 3. The chromatographic medium is in the form of a cylindrical plug 30 which is closely received within the cylindrical bore 6 of the chamber between an underlying cylindrical frit 31 and an overlying cylindrical frit 32. The frits 31 and 32 are typically nylon filters which are closely received in the cylindrical bore 6 so that the cylindrical surfaces of the chromatographic plug 30 and frits 31 and 32 make face-to-face contact with the bore 6. The plug 30 is retained in the bottom of the chamber 3 by abutment of the lower frit 31 against the internal shoulder formed by the annular flange 8. In practice it is likely that the test tray 1 will be commercially available with selective chromatographic mediums 30 and frits 31, 32 fitted so that the trays will be purchased as appropriate for an intended assay. As an alternative to a plug, the chromatographic medium can be inserted in the chambers in powder, slurry or other form.

Predetermined volumes of test liquid or liquids which are to be analysed are piperred or otherwise deposited in each of the chambers 3 so that such liquid in its flow through the chambers 3 is subjected to the chromatographic medium 30 in that chamber and the liquid emerging from the outlet ports 5, the percolate or eluate as the case may be, is collected in the respective wells 16 to be available for analysis. The trays of the assembly are particularly intended to be suitable for handling by automatic equipment where it is likely that the test liquid or liquids will be piperred simultaneously into the eight chambers A to B of the first column and the remaining columns of chambers are then successively charged with the test liquid. The frusto conical part 7 of the chamber 3 is desirable to provide a relatively large reservoir for the test In conducting a chromatographic assay it will often be essential to identify the wells 16 into which the percolate or eluate (as the case may be) has been collected from the chambers 3 which respectively communicate with those wells. For this purpose the collection tray 72 will conveniently be orientated so that the identification grid of letters A to H and numerals 1 to 12 correspond between the overlying trays and the references by which a particular chamber 3 identified are the same as those for identifying the well 16 with which that chamber communicates. To ensure that this orientation is achieved, co-operating means may be provided between the test and collection trays so that such means inter-engages when the trays are correctly orientated to be mounted one on the other (as shown in FIG. 2) but will not permit such mounting when the trays are incorrectly orientated with respect to each other. The co-operating means may simply comprise a track and track follower formed at corresponding corners of the test tray and the collection tray (as indicated at 40 in FIG. 2) and which track and track follower must inter-engage as the test tray is fitted to the top of the collection tray to permit the correct mounting. As an addition, or alternatively, where the trays are intended to be handled by automatic equipment, the equipment may be programmed to sense the presence or absence of a particular location on the trays from which their correct orientation relative to the equipment and to each other may be determined for example corresponding corners of the trays may be provided with upstanding chamfers or flats 41 on their respective side walls which are intended to be sensed by automatic handling equipment to ensure that the two trays are correctly orientated with respect to each other.

As the percolate or eluate liquid resulting from a chromatographic assay is collected in the wells 16, it will be appreciated from FIG. 2 that the penetration of the tubular spigots 12 into the mouths of the respective wells alleviates the possibility of cross contamination between the liquids which emerge from the respective outlet ports 5. Furthermore the volume of each well 16 below the level of the bottom end face of the tubular spigot which it receives is sufficient to accommodate all of the percolate ok eluate liquid which results from the respective chambers 3. Desirably therefore the aforementioned volume of each well is greater than the volume of each chamber 3 (although it is appreciated that the volume of test liquid which is deposited in each chamber 3 will often be the same as or less than the volume of the chamber 3 above the level of the uppermost frit 32). With such an arrangement it may be ensured that all of the percolate or eluate liquid from the chambers 3 can be accommodated within the respective wells 16 clear of the tubular spigots 12 in those wells. Consequently when the test tray is removed from the collection tray for analysis of the percolate or eluate, the possibility is alleviated of cross contamination by liquid on a tubular spigot inadvertently dripping into a well other than that within which the spigot was received.

The test and collection trays may be subjected to centrifugal forces and/or gas or air pressure differentials to promote the rate of liquid flow through the separation medium.

We claim:

1. An assay tray assembly comprising a one piece plastics moulded test tray removably mounted in overlying relationship in engagement with a plastics moulded collection tray; the test tray having a spaced array of discrete identical upstanding chambers to accommodate a predetermined volume of liquid for analysis, each chamber being formed with a top opening and a cylindrical lower part length which communicates with a bottom opening for the flow therethrough of the liquid, said bottom opening being formed as an outlet port by an inwardly directed annular flange provided in a downwardly projecting tubular spigot for the respective chamber; each said chamber carrying in its cylindrical lower part length a separation medium to which the liquid is to be subjected during its said through-flow and which separation medium is in cylindrical face-to-face contact with the cylindrical lower part of the chamber in which it is carried and is retained in that chamber by abutment with said flange; the collection tray having discrete upstanding wells each with an upwardly opening mouth, said wells corresponding in number to the chambers and having their mouths disposed in a spaced array corresponding to that of the tubular spigots; the tubular spigots being received one in each of said well mouths with the outlet ports of the respective chambers located centrally in the respective well mouths for the respective wells to collect liquid emanating from the chambers and to alleviate cross contamination between such liquids and wherein abutment means is provided between the trays to restrict the depth of entry of the tubular spigots into the wells whereby the volume of a liquid which is received by a well from the chamber communicating with that well is less than the volume of each well below the tubular spigot it receives.

2. An assembly according to claim 1 in which the separation medium is sandwiched in the lower part length of its respective chamber between underlying and overlying frits and is retained in that chamber by abutment of the underlying frit with the inwardly directed flange.

3. An assembly according to claim 2 in which the frits are in cylindrical face-to-face contact with the cylindrical lower part length of the chamber within which they are received.

4. An assembly according to claim 1 in which each chamber has an upper part length within which is located the top opening, said upper part length being frusto conical to converge as it approaches the bottom opening from the top opening and being co-axial with the cylindrical lower part length of the respective chamber.

5. An assembly according to claim 1 in which the separation medium is in the form of a substantially rigid or non-resilient cylindrical slug.

6. An assay tray comprising a one piece plastics moulded test tray having a spaced array of discrete identical upstanding chambers to accommodate a predetermined volume of liquid for analysis, each chamber being formed with a top opening and a cylindrical lower part length which communicates with a bottom opening for the flow therethrough of the liquid, said bottom opening being formed as an outlet port by an inwardly directed annular flange provided in a downwardly projecting tubular spigot for the respective chamber; each said chamber carrying in its cylindrical lower part length a separation medium to which the liquid is to be subjected during its said through-flow and which separation medium is in cylindrical face-to-face contact with the cylindrical lower part of the chamber in which it is carried and is retained in that chamber by abutment with said flange.

* * * * *

UNITED STATES PATENT AND TRADEMARK OFFICE
CERTIFICATE OF CORRECTION

PATENT NO. : 5,417,923
DATED : May 23, 1995
INVENTOR(S) : Dejan Bojanic et al.

It is certified that error appears in the above-identified patent and that said Letters Patent is hereby corrected as shown below:

On the title page under item. [53] "Related US Application Data", please insert the following foreign application priority data as item [30]:

— [30] Foreign Application Priority Data
April 25, 1990 [GB] United Kingdom ....... 9009308.9 —.

Signed and Sealed this

Eleventh Day of March, 1997

BRUCE LEHMAN

Attest:

Attesting Officer

Commissioner of Patents and Trademarks